US008677679B2

(12) United States Patent
Black et al.

(10) Patent No.: US 8,677,679 B2
(45) Date of Patent: Mar. 25, 2014

(54) AMPOULE FOR THE STORAGE AND DISPERSION OF VOLATILE LIQUIDS

(75) Inventors: Bruce C. Black, Yardley, PA (US); Shreya J. Shah, Lawrenceville, NJ (US); Linda A. Varanyak, Mercerville, NJ (US); Keith F. Woodruff, Mountainside, NJ (US)

(73) Assignee: FMC Corporation, Philadelphia, PA (US)

(*) Notice: Subject to any disclaimer, the term of this patent is extended or adjusted under 35 U.S.C. 154(b) by 349 days.

(21) Appl. No.: 12/872,277

(22) Filed: Aug. 31, 2010

(65) Prior Publication Data

US 2011/0072711 A1    Mar. 31, 2011

Related U.S. Application Data

(60) Provisional application No. 61/246,373, filed on Sep. 28, 2009.

(51) Int. Cl.
*A01M 1/10* (2006.01)
*A01M 1/02* (2006.01)

(52) U.S. Cl.
USPC ............... 43/123; 43/107; 43/132.1; 43/125; 239/44; 239/51.5; 239/53; 239/55; 239/57; 261/104; 261/DIG. 65; 261/DIG. 88

(58) Field of Classification Search
USPC ............... 43/132.1, 124, 125, 129, 123, 107; 239/34, 44, 51.5, 53, 55, 57; 261/104, 261/100, 101, DIG. 65, DIG. 88, 72.1; 392/390, 394, 403
See application file for complete search history.

(56) References Cited

U.S. PATENT DOCUMENTS 1,944,375 A * 1/1934 Schneider .................. 239/43
2,219,959 A * 10/1940 Laidley ..................... 239/57
(Continued)

FOREIGN PATENT DOCUMENTS

WO  WO 2005/096824 A1  10/2005
WO  WO 2008/095016 A2  8/2008

OTHER PUBLICATIONS

Storgard Insect Monitoring Systems, Advertisement Flyer, Trece, Inc. Aclair, OK, USA, Copyright 2007, [online: http://www.trece.com/stormon.html] 1 page.

(Continued)

*Primary Examiner* — Darren W Ark
(74) *Attorney, Agent, or Firm* — FMC Corporation (57) ABSTRACT

In one aspect, the present invention is directed to an ampoule for the storage and dispersion of a volatile liquid comprised of (a) an outer shell composed of an impermeable material and defining at least one opening; (b) a porous diffusion member defining an internal reservoir positioned inside said outer shell; (c) a volatile liquid contained within such internal reservoir; and (d) a film member adhered to the outer shell and covering the at least one opening; wherein the film member is disposed such that an air space is present between the porous diffusion member and the film member; and wherein the porous diffusion member is configured such that molecules of the volatile liquid can only enter into the air space via diffusion through the porous diffusion member. Such ampoules are particularly suited for the storage and dispersion of organic chemicals useful as bed bug attractants, such as a $C_8$-$C_{12}$ alkane. In another aspect, this invention is directed to a device adapted to receive one or more of such ampoules. In one preferred embodiment, such device is a bed bug capturing device.

9 Claims, 4 Drawing Sheets

(56) References Cited

U.S. PATENT DOCUMENTS

| | | | | |
|---|---|---|---|---|
| 2,412,326 A | * | 12/1946 | Dupuy | 239/51.5 |
| 2,766,066 A | * | 10/1956 | Hopson et al. | 239/44 |
| 2,819,135 A | * | 1/1958 | Shapiro | 239/44 |
| 3,016,199 A | * | 1/1962 | Keydel | 239/55 |
| 3,447,907 A | * | 6/1969 | Bennett | 239/51.5 |
| 3,951,622 A | * | 4/1976 | Wilk | 239/34 |
| 4,017,030 A | * | 4/1977 | Coplan et al. | 43/129 |
| 4,157,787 A | * | 6/1979 | Schwartz | 261/DIG. 88 |
| 4,165,835 A | * | 8/1979 | Dearling | 239/51.5 |
| 4,413,779 A | * | 11/1983 | Santini | 239/44 |
| 4,544,592 A | * | 10/1985 | Spector | 261/DIG. 88 |
| 4,583,686 A | * | 4/1986 | Martens et al. | 239/51.5 |
| 4,614,299 A | * | 9/1986 | Van Loveren et al. | 239/56 |
| 4,809,912 A | * | 3/1989 | Santini | 239/57 |
| 4,860,953 A | * | 8/1989 | Hsien | 239/55 |
| 4,890,791 A | * | 1/1990 | Hoffman | 239/44 |
| 4,898,328 A | * | 2/1990 | Fox et al. | 239/34 |
| 4,908,977 A | * | 3/1990 | Foster | 43/107 |
| 4,915,301 A | * | 4/1990 | Munteanu | 239/55 |
| 4,917,301 A | * | 4/1990 | Munteanu | 239/57 |
| 4,995,555 A | * | 2/1991 | Woodruff | 239/55 |
| 5,014,913 A | * | 5/1991 | Hoyt et al. | 239/57 |
| 5,060,858 A | * | 10/1991 | Santini | 239/57 |
| 5,121,881 A | * | 6/1992 | Lembeck | 239/44 |
| 5,230,867 A | * | 7/1993 | Kunze et al. | 239/57 |
| 5,575,992 A | * | 11/1996 | Kunze | 239/34 |
| 5,749,519 A | * | 5/1998 | Miller | 239/44 |
| 5,749,520 A | * | 5/1998 | Martin et al. | 239/44 |
| 5,840,246 A | * | 11/1998 | Hammons et al. | 239/55 |
| 5,875,968 A | * | 3/1999 | Miller et al. | 239/44 |
| 5,907,923 A | * | 6/1999 | Heath et al. | 43/107 |
| 5,975,427 A | * | 11/1999 | Harries | 239/34 |
| 6,029,900 A | * | 2/2000 | Quinones | 239/57 |
| 6,109,537 A | * | 8/2000 | Heath | 239/57 |
| 6,109,539 A | * | 8/2000 | Joshi et al. | 239/57 |
| 6,419,163 B1 | * | 7/2002 | Joshi et al. | 239/57 |
| 6,484,438 B2 | * | 11/2002 | Matsunaga et al. | 43/129 |
| 6,569,907 B1 | * | 5/2003 | Kubo et al. | 239/60 |
| 6,625,922 B1 | * | 9/2003 | Ernsberger, IV | 43/107 |
| 6,769,631 B2 | * | 8/2004 | Brown | 239/57 |
| 6,821,526 B1 | * | 11/2004 | Huang | 43/122 |
| 6,854,208 B1 | * | 2/2005 | Chuang et al. | 43/125 |
| 7,000,852 B1 | * | 2/2006 | Chiu | 239/53 |
| 7,249,719 B2 | * | 7/2007 | He et al. | 239/44 |
| 7,309,024 B2 | * | 12/2007 | Hansen et al. | 239/44 |
| 7,379,662 B2 | * | 5/2008 | Caserta et al. | 239/34 |
| 7,548,684 B2 | * | 6/2009 | Berrido et al. | 392/394 |
| 7,591,099 B2 | * | 9/2009 | Lang et al. | 43/107 |
| 7,670,566 B2 | * | 3/2010 | Adair et al. | 422/125 |
| 7,712,248 B2 | * | 5/2010 | Beroza | 43/107 |
| 7,793,861 B2 | * | 9/2010 | Bankers et al. | 239/44 |
| 7,892,528 B2 | * | 2/2011 | Siljander et al. | 424/84 |
| 7,913,449 B2 | * | 3/2011 | Beroza | 43/107 |
| 7,959,132 B2 | * | 6/2011 | Butler et al. | 261/104 |
| 7,988,984 B2 | * | 8/2011 | Hockaday | 43/132.1 |
| 8,048,379 B2 | * | 11/2011 | Sassoon | 43/125 |
| 8,119,064 B2 | * | 2/2012 | Woo et al. | 239/57 |
| 8,146,290 B1 | * | 4/2012 | Telly | 43/123 |
| 8,211,419 B2 | * | 7/2012 | Siljander et al. | 424/84 |
| 8,266,839 B2 | * | 9/2012 | Bernard | 43/131 |
| 2005/0091911 A1 | * | 5/2005 | Matts et al. | 43/131 |
| 2005/0191481 A1 | * | 9/2005 | He et al. | 428/304.4 |
| 2005/0199742 A1 | * | 9/2005 | Maat | 239/44 |
| 2006/0233538 A1 | * | 10/2006 | Tollens et al. | 239/34 |
| 2007/0044372 A1 | | 3/2007 | Lang et al. | |
| 2008/0011871 A1 | * | 1/2008 | Sexton | 239/55 |
| 2008/0148624 A1 | * | 6/2008 | Borth et al. | 43/132.1 |
| 2008/0168703 A1 | | 7/2008 | Siljander et al. | |
| 2008/0276523 A1 | * | 11/2008 | McKechnie | 43/129 |
| 2009/0000180 A1 | * | 1/2009 | Palencia-Adrubau et al. | 43/131 |
| 2009/0145019 A1 | * | 6/2009 | Nolen et al. | 43/123 |
| 2009/0145020 A1 | * | 6/2009 | McKnight | 43/123 |
| 2009/0175604 A1 | * | 7/2009 | Ji et al. | 392/403 |
| 2009/0223115 A1 | * | 9/2009 | Lang et al. | 43/123 |
| 2009/0260276 A1 | * | 10/2009 | Kirsch et al. | 43/123 |
| 2010/0154290 A1 | * | 6/2010 | Fisher | 43/107 |
| 2010/0212213 A1 | * | 8/2010 | Hope et al. | 43/123 |
| 2011/0044936 A1 | * | 2/2011 | Black et al. | 424/84 |
| 2011/0047860 A1 | * | 3/2011 | Black et al. | 43/123 |
| 2011/0072712 A1 | * | 3/2011 | Black et al. | 43/123 |
| 2011/0203159 A1 | * | 8/2011 | Mcknight | 43/123 |
| 2011/0253801 A1 | * | 10/2011 | Buschmann | 239/57 |
| 2011/0266359 A1 | * | 11/2011 | Haran | 239/34 |
| 2011/0289824 A1 | * | 12/2011 | Wu et al. | 43/132.1 |
| 2011/0303757 A1 | * | 12/2011 | Blondeau et al. | 239/34 |
| 2012/0080537 A1 | * | 4/2012 | Walter | 239/34 |
| 2012/0104113 A1 | * | 5/2012 | Abfall et al. | 239/57 |
| 2012/0110894 A1 | * | 5/2012 | Black et al. | 43/123 |
| 2012/0141353 A1 | * | 6/2012 | Black et al. | 423/438 |
| 2012/0246998 A1 | * | 10/2012 | Vasudeva et al. | 43/123 |
| 2012/0285076 A1 | * | 11/2012 | Banfield | 43/123 |

OTHER PUBLICATIONS

Silvandersson Sweden AB, Silvatronic Bug Dome, [online: http://www.silvandersson.se/en/hotel-restaurant/hotel-restaurant.html], 2 pages.

McKnight S., Biosenory, Inc. Putnam, CT, USA, 'Traps and Attractants for Monitoring Bed Bug Infestations', Wang, et al., Purdue University, Dept. of Entomology, West Lafayette, IN, USA. [online: www.sternenvironmental.com/pdfs/Purdue-Presentation-12-07.ppt] 17 pages.

Wang, C., et al., 'Bed Bug (Heteroptera: Cimicidae) Attraction to Pitfall Traps Baited with Carbon Dioxide, Heat and chemical Lure', Journal of Econ. Entomol. 102(4); pp. 1580-1585, 2009.

Siljander, E., et al., 'Identification of the Airborne Aggregation Pheromone of the Common Bed Bug, Cimex lectularius', Journal of Chem. Ecol. 34: pp. 708-718, 2008.

* cited by examiner

AMPOULE FOR THE STORAGE AND DISPERSION OF VOLATILE LIQUIDS

FIELD OF THE INVENTION

The invention relates to novel volatile liquid storage ampoules useful, for example, for the storage and eventual controlled dispersion of volatile liquids.

BACKGROUND OF THE INVENTION

Bed bugs are small nocturnal insects of the family Cimicidae that feed off the blood of humans and other warm blooded hosts. Bed bugs exhibit cryptic behavior, which makes their detection and control difficult and time consuming. This is particularly true for the common bed bug, *Cimex lectularius*, which has become well adapted to human environments. Other species of bed bugs are nuisances to people and/or animals as well.

While bed bugs have been controlled in many areas, such as the United States, the increase in international travel has contributed to a resurgence of these pests in recent years. There are many aspects of bed bugs which make it difficult to eradicate them once they have established a presence in a location. Accordingly, there is a need for effective traps to determine the presence of bed bugs before they become entrenched.

Adult bed bugs are about 6 millimeters long, 5 to 6 millimeters wide, and are reddish brown with oval, flattened bodies. The immature nymphs are similar in appearance to the adults, but are smaller and lighter in color. Bed bugs do not fly, but can move quickly over surfaces. Female bed bugs lay their eggs in secluded areas and can deposit up to five eggs per day, and as many as 500 during a lifetime. The bed bug eggs are very small, about the size of a dust spec. When first laid, the eggs are sticky causing them to adhere to surfaces.

Bed bugs can go for long periods of time without feeding. Nymphs can survive for weeks without feeding, while adults can survive for months. Consequently, infestations cannot be eliminated simply by leaving a location unoccupied for brief periods of time. Further, such feeding habits make it difficult to monitor whether bed bugs are present as they may only be attracted to bait when hungry. Thus, in order to be effective, a bed bug capturing device must be able to generate attractants at an effective concentration for an extended period of time.

While bed bugs are active during the nighttime, during daylight they tend to hide in tiny crevices or cracks. Bed bugs may therefore find easy hiding places in beds, bed frames, furniture, along baseboards, in carpeting and countless other places. Bed bugs tend to congregate but do not build nests like some other insects.

Bed bugs obtain their sustenance by drawing blood through elongated mouth parts. They may feed on a human for 3 to 10 minutes, although the person is not likely to feel the bite. After the bite, the victim often experiences an itchy welt or a delayed hypersensitivity reaction resulting in a swelling in the area of the bite. However, some people do not have any reaction or only a very small reaction to a bed bug bite. Bed bug bites have symptoms that are similar to other pests, such as mosquitoes and ticks. It is not possible to determine whether a bite is from a bed bug or another type of pest; and bites may be misdiagnosed as hives or a skin rash. Consequently, bed bug infestations may frequently go on for long periods before they are recognized.

Bed bug infestations originate by a bed bug being carried into a new area. Bed bugs are able to cling to possessions and hide in small spaces, such that they may be transported in a traveler's belongings. As a result, buildings where the turnover of occupants is high, such as hotels, motels, inns, barracks, cruise ships, shelters, nursing homes, camp dwellings, dormitories, condominiums and apartments, are especially vulnerable to bed bug infestations.

Because of all the features of bed bugs described herein, bed bugs are both difficult to detect and eradicate. Professional pest removal specialists and pesticides are needed. It is necessary to remove all clutter and unnecessary objects from a room, remove bed bugs and eggs as much as possible through vacuuming, and apply pesticides to likely hiding areas. This type of treatment for eradication can be disruptive to a business such as a hotel. As a result, it is desirable to detect bed bugs at the earliest possible moment before an infestation becomes established.

The tiny, mobile and secretive behavior of bed bugs makes it nearly impossible to prevent and control an infestation unless they are quickly discovered and treated. Bed bugs have been found to move through holes in walls, ceilings and floors into adjacent rooms. Devices and methods for the early detection of bed bugs are especially needed in the hospitality industries.

Many attempts have been made to devise bed bug monitoring and/or capture devices in the past. Several of these devices employ pheromones, human sweat components or other organic chemicals which are heavier than air as lures in order to attract bed bugs to their trapping mechanism.

Thus, U.S. Patent Application 2008/0168703 A1 discloses a chemical formulation which is capable of attracting bed bugs when volatized comprising a mixture of chemicals found in bedbug pheromones including a monoterpene, a saturated aldehyde, an unsaturated aldehydes and a ketone.

Somewhat similarly, U.S. Patent Application 2007/0044372 discloses components of breath, perspiration and hair or skin oil which may be employed as bed bug olfactory attractants.

However, devices employing such heavier than air organic chemical attractants have, in general, not proven to be commercially effective. The present inventors have studied many aspects of bed bug behavior, and believe that one factor in the failure of such devices to desirably perform is the failure of such devices to disperse such attractants at a constant rate which will be attractive to bed bugs. Thus it has been observed by the present inventors that there are optimal concentrations of such chemical attractants in terms of luring bed bugs to traps. Too low a concentration will be insufficient to attract bed bugs; conversely, at too high of a concentration, such "attractants" were found to have a repellent effect. Accordingly, in order for a bed bug monitor to be effective, it is necessary that such monitor release attractants at a desired rate for a substantial period of time, frequently for a week or more.

For several of the most effective bed bug attractants, including pheromones such as hexenal and octenal, and human sweat components such as butyric acid, it has been found that a very low rate of diffusion is optimal for attracting bedbugs. Specifically, in order to be most attractive to bedbugs, the optimal concentration of the Hexenal and Octenal mixture to be released is from about 50 ng/L/hr to about 200 ng/L/hour, and the optimal concentration of butyric acid to be released is between about 15 ng/L/hr and about 50 ng/L/hr. However, in order to avoid decomposition issues, such attractants are typically formulated in volatile organic solvents such as $C_8$-$C_{12}$ alkanes. Unfortunately, such solvents are so volatile that when exposed to air they quickly evaporate, resulting in a too-high initial release rate of attractants (which may in fact repel bed bugs). Further, this rapid release may quickly deplete the attractants from the monitor, with the result that after such high initial burst, the release rate is too low to effectively attract bed bugs.

Accordingly, there is a need for a means to release such attractants at a steady predetermined rate for an extended period of time.

In addition to the bed bug attractants discussed above, there is a similar need for the sustained, measured release of other materials including perfumes, air fresheners, aroma therapy components, pesticides, repellants and pharmaceuticals.

SUMMARY OF THE INVENTION

In one aspect, the present invention is directed to an ampoule for the storage and dispersion of a volatile liquid comprised of (a) an outer shell composed of an impermeable material and defining at least one opening; (b) a porous diffusion member defining an internal reservoir positioned inside said outer shell; (c) a volatile liquid contained within such internal reservoir; and (d) a film member adhered to said outer shell and covering said at least one opening; wherein said film member is disposed such that an air space is present between said porous diffusion member and said film member; and wherein said porous diffusion member is configured such that molecules of the volatile liquid can only enter into said air space via diffusion through said porous diffusion member. Such ampoules are capable of releasing a volatile chemical at a constant rate for an extended period of time, including at very low zero order of magnitude rates. Accordingly, they are particularly suited for the storage and dispersion of organic chemicals useful as bed bug attractants, especially where such attractants are formulated in a highly volatile liquid, such as a $C_8$-$C_{12}$ alkane.

In another aspect, this invention is directed to a device adapted to receive one or more of such ampoules. In one preferred embodiment, such device is a bed bug capturing device.

DETAILED DESCRIPTION OF THE INVENTION

In one aspect, the present invention is directed to an ampoule for the storage and dispersion of a volatile liquid comprised of (a) an outer shell composed of an impermeable material and defining at least one opening; (b) a porous diffusion member defining an internal reservoir positioned inside said outer shell; (c) a volatile liquid contained within such internal reservoir; and (d) a film member adhered to said outer shell and covering said at least one opening; wherein said film member is disposed such that an air space is present between said porous diffusion member and said film member; and wherein said porous diffusion member is configured such that molecules of the volatile liquid can only enter into said air space via diffusion through said porous diffusion member.

The outer shell of the ampoule of this invention may be of any configuration so long as it (1) is adapted to contain the porous diffusion member; and (2) defines at least one opening which is adapted to be covered by the film member. Conveniently, such shell is in the shape of a cylinder although, as will be apparent to one of skill in the art, other configurations may be employed as well.

The outer shell may be composed of any material which is impervious to the liquid stored within the porous diffusion member and/or in the internal reservoir defined therein. Thus, for example, when such liquid comprises a highly volatile solvent such as a $C_8$-$C_{12}$ alkane (which may be employed in conjunction with bed bug attractants including octenal, hexenal and butyric acid) such outer shell may be made of metal, glass or resistant plastics such as polyethylene terephthalate.

The porous diffusion member is configured such that, when placed within the outer shell, it defines an internal reservoir. Due to such configuration, liquid placed within such reservoir is prohibited from passing beyond such diffusion member (e.g., into the air space defined between the diffusion member and the film member) except via diffusion through the porous diffusion member. Such configuration permits the ampoule to be positioned in any manner (such as sideways, upside down, etc.) without affecting the release rate of the liquid from the ampoule.

The porous diffusion member is typically composed of a non-deformable, sintered, porous synthetic resin having a controlled porosity and having omni-directional interconnecting pores, formed of aggregates of united polymer particles. The degree of porosity of the porous materials can be controlled in their manufacture, thus insuring a wide range of porosity to suit a wide range of liquid products of varying viscosities. Thus, for example, the porous diffusion member may be fabricated of high-density polyethylene, low-density polyethylene, ultra-high molecular weight polyethylene, polypropylene, polyvinylidene fluoride, and the like. Products are available commercially under the trade designations "Porex" porous plastics and "Porous poly." When the volatile liquid comprises a $C_8$-$C_{12}$ alkane, the porous diffusion member is preferably composed of ultra high molecular weight polyethylene.

The pore size of the diffusion member may vary widely, depending on the liquid to be delivered. For highly volatile liquids such as $C_8$-$C_{12}$ alkanes, smaller pore sizes of about one micron or less are preferred, although for other liquids the pore size may vary between about one to 200 microns.

The film member is adhered to the outer shell and positioned such that (a) it covers the at least one opening defined by the outer shell; and (b) an air space is formed between the porous diffusion member and such film member.

In one embodiment of this invention, the film member is composed of a permeable substance which will permit molecules of the liquid contained within the internal reservoir which have diffused through the porous diffusion member into air space to exit the ampoule into the ambient environment.

In another embodiment, the film member is composed of an impermeable film (e.g., a metal film, such as aluminum foil) which will prohibit diffused molecules from exiting the ampoule until one or more holes in such film member are produced. Such holes may be produced by puncturing the film member or by removing a seal which covers pre-existing hole(s) in such film member.

The film member may be adhered to the outer shell by any means which will produce a seal such that the desired release rate of volatiles from the ampoule is not compromised. Specifically, adhesives and sealants which are susceptible to being dissolved and/or permeated by such volatiles should not be employed.

When such volatiles comprise a $C_8$-$C_{12}$ alkane, the film member is preferably adhered to the outer shell by heat sealing the film (preferably made of aluminum) to the outer shell (which is preferably made of polyethylene terephthalate). Due to safety concerns, such heat sealing should be done under a nitrogen blanket or a similarly inert atmosphere. In such embodiments, it is preferred that the outer shell have a flange around its upper rim in order to increase the surface area available for heat sealing.

The ampoules of this invention may be used to regulate the release of many types of volatile chemicals, including perfumes, air fresheners, aroma therapy components, pesticides, repellants, pharmaceuticals and the like. In one particularly preferred embodiment, such ampoules are particularly suitable for the storage and dispersion of organic chemicals used as bed bug attractants.

In order to achieve a relatively constant release of the volatile active material from the ampoule where a solvent is employed, the vapor pressure of the active material and of the solvent should be as close as possible, preferably of the same order of magnitude.

Bed bug attractants which may be employed include pheromones, human sweat components and the like. Specific attractants which can be employed include bed bug pheromone components including monoterpenes (such as (+)-limonene and (−)-limonene); saturated aldehydes (such as nonanal and decanal), unsaturated aldehydes (such as (E)-2-hexenal, (E)-2-octenal, (E,E)-2,4-octadienal, and (E,Z)-2,4-octadienal), aromatic aldehydes (such as benzaldehyde), ketones (such as sulcatone and geranylacetone), acetates (such as benzyl acetate), aromatic alcohols (such as benzyl alcohol); human breath components (such as methanol, methane, furan, and pyridine); human perspiration components (including lactic acid, butyric acid, octenol, indole, 6-methyl-5-hepten-2-one, geranyl acetone, 1-dodecanol, 3-methyl-1-butanol, carboxylic acids, and urea); and human skin oil components such as sebum. Mixtures of one or more attractants may also be employed.

One attractant combination which is particularly preferred is a composition comprising an unsaturated aldehyde component and an organic acid component. It is preferred that the unsaturated aldehyde component be comprised of one or more aldehydes selected from the group consisting of trans-2-hexen-1-al (Hexenal) and trans-2-octen-1-al (Octenal). It is preferred that the organic acid component be butyric acid. When the aldehyde component is comprised of both Hexenal and Octenal, it is preferred that the aldehydes be present in a weight ratio of from about 1:5 and about 5:1 of Hexenal to Octenal, more preferably in a weight ratio of between about 3:1 and about 1:3. In order to be most attractive to bedbugs, the optimal concentration of the Hexenal and Octenal mixture to be released is from about 50 ng/L/hr to about 200 ng/L/hour, and the optimal concentration of butyric acid to be released is between about 15 ng/L/hr and about 50 ng/L/hr. Mixing butyric acid with Hexenal and Octenal forms an unstable composition and it is necessary to separate the aldehyde component from the acid component. In order for the separate components of the attractant composition to be released at the proper rates, each component may be dissolved in an organic solvent, for example a $C_8$-$C_{12}$ alkane. For applications in which the ampoule may be subjected to temperature fluctuations between about 20° C. and 40° C., decane and undecane are particularly preferred solvents as their rate of volatilization is less affected by such temperature fluctuations than is nonane.

An alternative preferred embodiment involves the use of Octenal and/or Hexenal alone; with or without the use of butyric acid as a co-attractant.

The ampoules of this invention may be adapted to include attractants for other insects as well. Thus, for example, the following table contains a list of attractants which may be included in the volatile liquid in order to attract the indicated species.

| Common Name | Specie | Attractant |
|---|---|---|
| Indianmeal Month | Plodia interpuntella | (Z,E)-9, 12-tetradecadien-1-ol acetate |
| Almond Moth | Cadra cautella | (Z,E)-9, 12-tetradecadien-1-ol acetate |
| Rasin moth | Cadra figulilella | (Z,E)-9, 12-tetradecadien-1-ol acetate |
| Tobacco Moth | Ephestia elutella | (Z,E)-9, 12-tetradecadien-1-ol acetate |
| Red flour beetle | Tribolium castaneum | 4,8-dimethyldecanal |
| Confused flour beetle | Tribolium confusum | 4,8-dimethyldecanal |
| Wharehouse beetle | Trogoderma variabile | 14-methy-Z8-hexadecen-1-al |
| Cabinet Beetle | Trogoderma versicolor | 14-methy-Z8-hexadecen-1-al |
| Larger Cabinet Beetle | Trogoderma inclusum | 14-methy-Z8-hexadecen-1-al |
| Cigarette beetle | Lasioderma serricorne | (4S,5R)-5-hydroxy-4-methyl-3-heptanone (Serricorne) |
| Sawtoothed grain beetle | Oryzeaphilus surinamensis | 1-octen-3 -ol&3-methylbutano1&11-methyl-(3Z,6Z)-dodecadien-11-olide (Wheat germ oil) |
| Merchant Grain Beetle | Oryzeaphilus mercator | 1-octen-3-ol&3-methylbutanol&11-methyl-(3Z,6Z)-dodecadien-11-olide (Wheat germ oil) |
| Rice Weevil | Sitophilus oryzae | 5-hydroxy-4-methyl-3-heptanone (Sitophilure) |
| Granery Weevil | Sitophilus granaries | 5-hydroxy-4-methyl-3-heptanone (Sitophilure) |
| Maize Weevil | Sitophilus zeamais | 5-hydroxy-4-methyl-3-heptanone (Sitophilure) |
| Lesser Grain Beetle | Rhyzopertha dominica | (S)-(+)-1-methylbutyl (E)-2-pentenoate and (S)-(+)-1-methylbutyl-(E)-2,4-dimethyl-2-pentenoate (Dominicalure 1&2) |
| Housefly | Musca domestica | (Z)-9-tricosene (Muscalure) |
| Olive Fly | Bactrocera oleae | Amonium bicarbonate, 1,7-dioxaspiro-(5,5) udecane (Spiroketal) |
| Stable fly | Stomoxys calcitrans | 15-methyltritriacantane; 15,19-dimethyltritriacantane; (Z)-9-hentriacontene; (Z)-9-tritriacontene; 13-methyl-hentriacontene; 13-methyl-1-tritriacontene |
| House Cricket | Acheta domesticus | Acetic acid, Isobutyric acid; Valeric acid; Isovaleric acid |
| Migratory Locust | Schistocerca gregaria | 2-Phenylacetonitrile |
| Western Corn Rootworm | Diabrotica virgifera | 1,2,4-Trimethoxybenzene; 1H-indole; E-cinnamaldehyde |
| Boll Weevil | Anthonomus grandis | Grandisol; Grandlure II; Grandlure III; Grandlure IV |
| Earwig | Forficula auricularia | 2-Ethyl-1,4-benzoquinone |
| Yellow Jacket/ European | Vespula germanica Vespula | Acetic acid; Heptyl butyrate; 2-Methylpropan-1-ol |

-continued

| Common Name | Specie | Attractant |
|---|---|---|
| Hornet | pensylvanica Vespula maculifrons Vespa crabro | |
| Paper Wasp | Polistes dominulus | Acetic acid; Heptyl butyrate; 2-Methylpropan-1-ol; Z5-tangerinol; E5-tangerinol; E,E-farnesyl acetate |
| Bald-faced Hornet | Dolichovespula maculata | Acetic acid; Heptyl butyrate; 2-Methylpropan-1-ol |
| Oriental Cockroach | Blattana orientalis | Glucanolactone; 1,4-Benzoquinone; p-Cresol; 2-Ethylphenol; Gluconic acid |
| German Cockroach | Blattana germanica | 3,11-dimethylnonacosan-2-one and Blattellaquinone |
| Corn Earworm | Heliocoverpa zea | (Z)-11-Hexadecenal |
| Tobacco Budworm | Heliothjis virescens | (Z)-11-Hexadecenal; (Z)-7-Hexadecenal; (Z)-9-Hexadecenal; Hexadecanal; (Z)-11-Hexadecen-1-ol; Tetradecanal; (Z)-9-Tetradecenal |
| Pink Bollworm | Pectinophora gossypiella | 10-propyl-trans-5,9-tridecadienyl acetate |
| Coddling Moth | Cydia pomonella | Codlemone |
| Navel Orange Worm | Amyelois transitella | (Z,Z)-11-13-hexadecadienyl acetate |
| Face Fly | Musca autumnalis | (Z)-14-nonacosene; (Z)-13-nonacosene; (Z)-13-heptacosene |
| Hessian Fly | Mayetiola destructor | (2S)-(E)-10-tridecen-2-yl acetate |
| Emerald Ash Borer | Agrilus planipennis | Cis-3-hexenal |
| Japanese Beetle | Popillia japonica | (Z)-5-(1-decenyl)dihydro-2(3H)-furanone |
| Armyworms | Spodoptera spp. | Z9-14 Ac; Z9E11-14 Ac; Z9E12-12 Ac |

The ampoules are typically assembled by providing the outer shell; dispensing the liquid comprising the volatile molecules into the outer shell; inserting the porous diffusion member into the outer shell; and adhering the film member across the at least one hole defined by the outer shell.

In another aspect, the present invention is directed to a device adapted to receive one or more of the ampoules of this invention. As will be readily apparent to one of skill in the art, the particular components and construction of such device will depend greatly upon its function as well as upon the volatile chemicals to be released from the ampoule.

In one preferred embodiment, the device of this invention is a bed bug capturing device. Such a bed bug capturing device will comprise, in addition to an ampoule receiving means, a trapping element capable of trapping bedbugs which are lured into the device by the release attractants. The trap element may comprise any means which will make it difficult or impossible for bed bugs to exit the trap once they have entered. Although sticky traps may be employed for this purpose, in general the use of such traps is not preferred in the absence of a heating element, as it has been observed that bed bugs will not be ensnared by certain adhesives which are effective to trap other insects.

Preferably, the trap element is a deadfall trap. In one particularly preferred embodiment, the trap element comprises at least one pathway comprising: (i) an upwardly sloped segment; (ii) a downwardly sloped segment; and (iii) a deadfall trap area: characterized in that the upwardly sloped segment and at least the outer portion of such inwardly sloped segment possesses an average surface roughness of at least about 2.5 micrometers, preferably of at least about 3.0 micrometers. The average surface roughness of a material can be measured using a Pocket Surf® portable surface roughness gage available from Mahr Federal Inc.

If desired, the trap area may contain an insecticide or a viscous liquid which will further immobilize or kill bed bugs.

In one preferred embodiment, the bed bug capturing device further comprises a means for puncturing hole(s) of a predetermined size and location through the film member of the ampoule such that the flow of volatile attractants from the ampoule occurs at a predetermined rate.

In another preferred embodiment, the bed bug capturing device further comprises a means for producing an air flow such that the air movement from the device has a face velocity of between about 5 and about 50 ml/cm$^2$/min. Preferably, such means produces an air flow such that the face velocity of air exiting the device is between about 10 and about 40 ml/cm$^2$/min.

Any means of producing such an air flow may be employed, including compressed air, air pumps, heating devices, nebulizers, fans and the like. Preferably the means of producing air flow is a fan.

The bed bug capturing device of this invention may be made of any suitable material or materials which do not repel bed bugs. Preferred materials include hard plastics such as high impact polyethylene or acrylonitrile butadiene styrene. Other materials which may be employed include polychlorotrifluoroethylene, polycarbonates, polyvinylidene chloride, high density polyethylene, cardboard, wax paper board, galvanized metal and aluminum.

It is preferred that the device be dark in color, for example black, dark gray, navy blue, dark blue or deep violet as bed bugs tend to choose darker surfaces over lighter surfaces. In general, colors darker than a photographic gray card are preferred.

The present invention may be better understood by reference to the attached Figures which are intended to be demonstrative of certain embodiments, but are not intended to be limiting of the scope of the invention in any manner.

Figure 1:
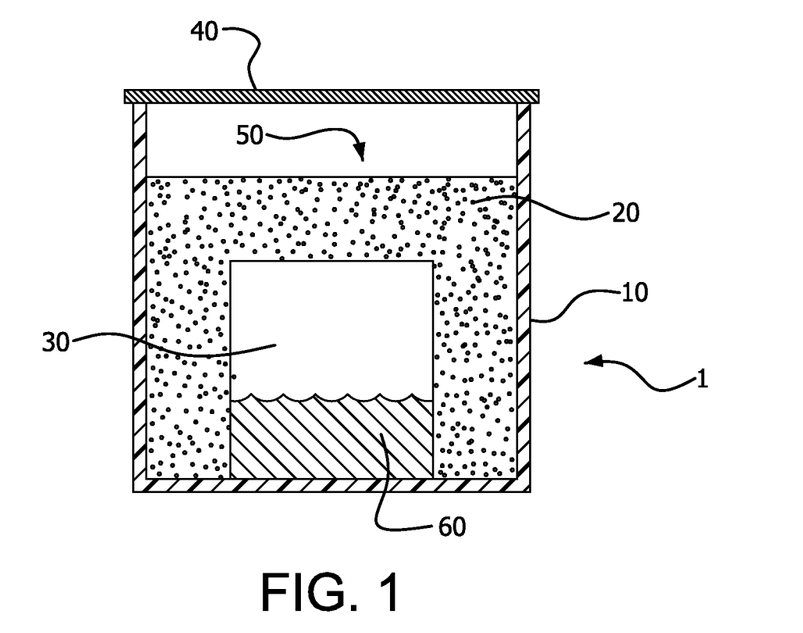
FIG. 1 is a cross-sectional view of one embodiment of the ampoule of this invention wherein the film member is a unitary sheet which extends across the at least one opening.

FIG. 1 is a cross-sectional view of one embodiment of the ampoule of this invention wherein the film member is a unitary sheet which extends across the at least one opening. Ampoule 1 is composed of outer shell 10 which defines at least one opening. Porous diffusion member 20, which defines interior reservoir 30, is inserted within outer shell 10. Film member 40 is disposed across the at least one opening defined by outer shell 10, such that air space 50 is defined between film member 40 and porous diffusion member 20. Liquid 60, which comprises one or more volatile chemicals, is disposed within internal reservoir 30.

Porous diffusion member 20 is configured such that molecules of liquid 60 can only enter into air space 50 via diffusion through porous diffusion member 20. Specifically, such diffusion member 20 is configured such that liquid 60 cannot leak directly into air space 50, e.g., by passing between diffusion member 20 and outer shell 10.

Volatile molecules contained in liquid 60 will diffuse through porous diffusion member 20 and into air space 50. In embodiments in which film member 40 is a permeable membrane, such molecules may diffuse directly through film member 40 and into the ambient environment. As will be appreciated by one of skill in the art, the diffusion rate of the volatile molecules through permeable film member 40 may be adjusted to a desired range by altering the thickness of such film member and/or its composition.

In embodiments in which film member 40 is impermeable to such molecules, one or more holes (not shown) may be created in film member 40 which will permit the release of such molecules from air space 50 into the ambient environment. By determining the precise dimensions of such one or more holes, such release rate may be set at a predetermined rate.

Figure 2:
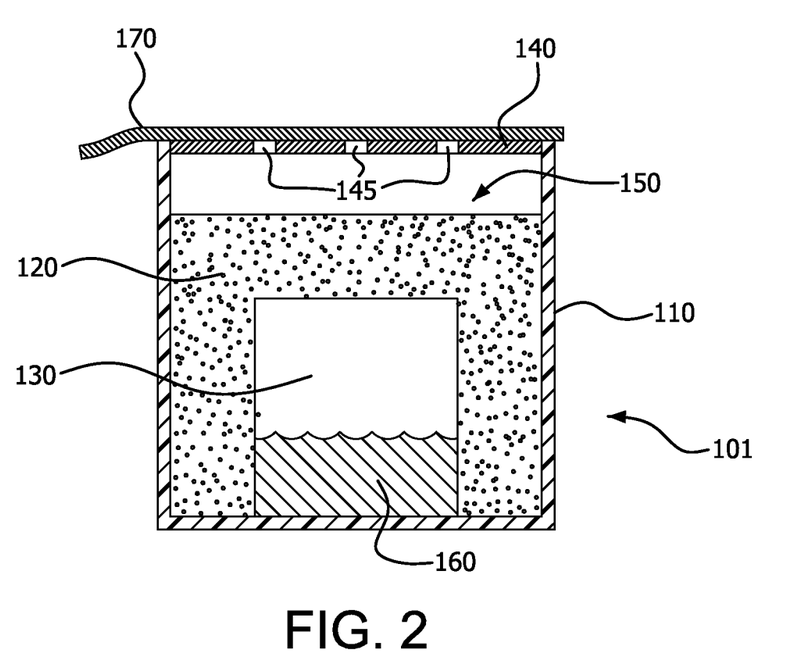
FIG. 2 is a cross-sectional view of a second embodiment of the ampoule of this invention wherein the film member contains one or more preformed apertures which are covered by a removable cover portion.

FIG. 2 is a cross-sectional view of a second embodiment of the ampoule of this invention wherein the film member contains one or more preformed apertures which are covered by a removable cover portion. Ampoule 101 is composed of outer shell 110 which defines at least one opening. Porous diffusion member 120, which defines interior reservoir 130, is inserted within outer shell 110. Film member 140 is disposed across the at least one opening defined by outer shell 110, such that air space 150 is defined between film member 140 and porous diffusion member 120. Liquid 160, which comprises one or more volatile chemicals, is disposed within internal reservoir 130. Preformed apertures 145 are defined within film member 140, but are initially sealed by removable cover portion 170.

Porous diffusion member 120 is configured such that molecules of liquid 160 can only enter into air space 150 via diffusion through porous diffusion member 120. Specifically, such diffusion member 120 is configured such that liquid 160 cannot leak directly into air space 150, e.g., by passing between diffusion member 120 and outer shell 110.

Volatile molecules contained in liquid 160 will diffuse through porous diffusion member 120 and into air space 150. Such molecules are trapped within air space 150 until the removal of cover portion 170, when then such molecules to pass through apertures 145 into the ambient atmosphere. By controlling the area of apertures 145, the rate of such diffusion can be controlled.

Figure 3:
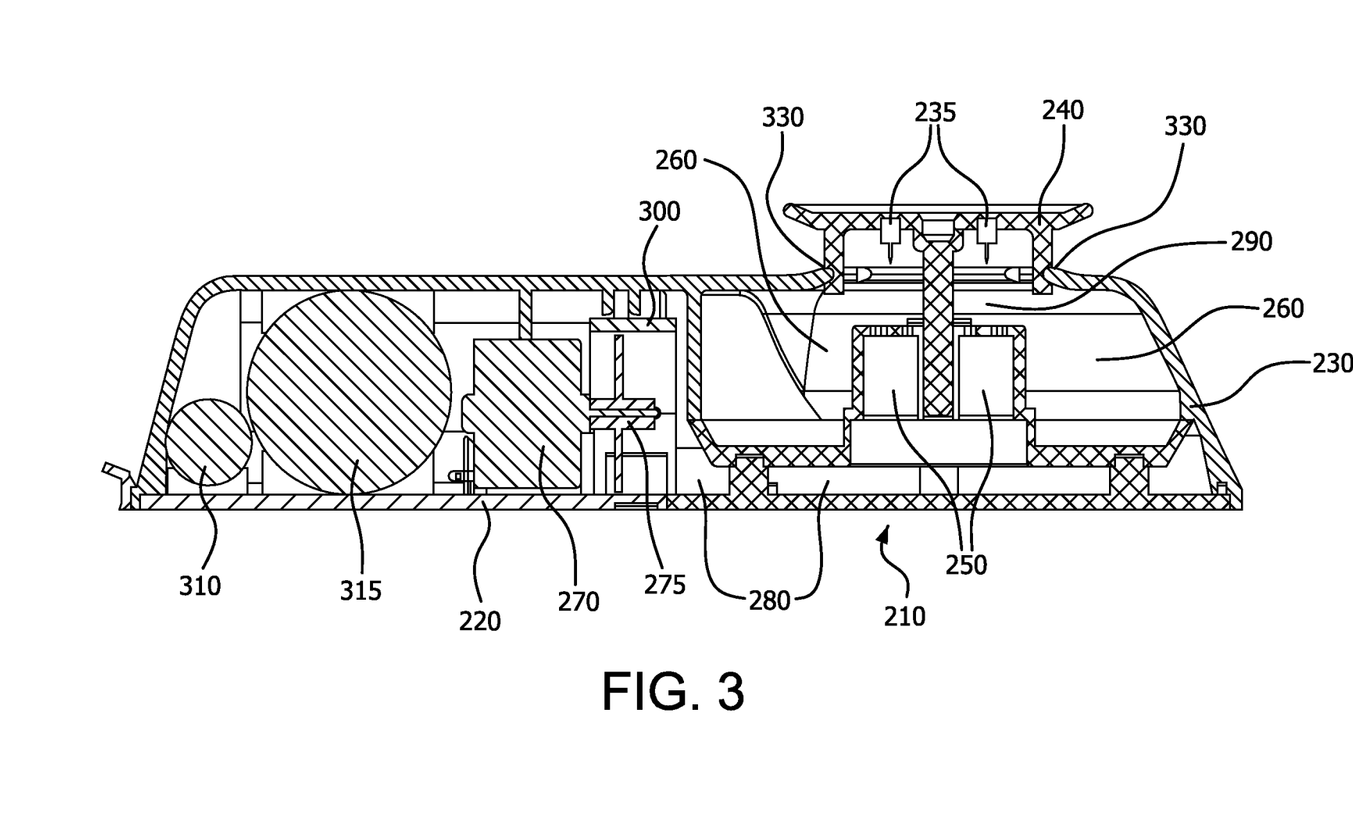
FIG. 3 is a cross-section of a device of this invention which is adapted to receive the ampoule of this invention, which device is a bed bug capturing device.

FIG. 3 is a cross-section of a device of this invention which is adapted to receive the ampoule of this invention, which device is a bed bug capturing device comprising a means for creating a puncture of a predetermined size in the film member of such a received ampoule. Bed bug capturing device 210 comprises base member 220, top member 230 and activation member 240. Ampoule receptor means 250 are defined within device 210, and are located within deadfall trap area 260. Fan unit 270, comprising propeller 275 is disposed such that air created by the movement of propeller 275 will be forced into channel 280 and then through holes (not shown in this FIGURE) connecting channel 280 into air space 290. Baffle 300 is disposed around propeller 275 in order to provide a more consistent air flow. Fan 270 is powered by batteries 310 and 315. Although two batteries are shown in this embodiment, it will be recognized that a single battery may be employed. Activation member 240 contains pins 235 which are disposed such that pressing (or in other embodiments turning) activation member 240 will result in such pins puncturing the film member of an ampoule inserted into such a device, creating hole(s) of a predetermined size. After creating such punctures activation means 240 is raised, e.g. by a spring mechanism or by turning such member is the opposite direction from that required to lower the puncturing means. Activation member 240 may also be designed, by means well known to one of skill in the art, to complete a circuit upon being raised, causing fan 270 to begin operating via a connection to batteries 310 and 315.

Once the film member of an ampoule placed into the device has been punctured, volatile molecules (such as bed bug attractants and their carriers) will diffuse out of the ampoule and into air space 290. Moving air created by fan 270 will pass into air space 290 via channel 280 (as discussed above) and will carry such molecules out of the trap by channels (not shown) located above lip 330 of top member 230. Such channels will additionally serve as an entry means for bed bugs, lured by the diffusion of the attractant molecules at a steady pre-determined rate, into the trap area 260 of the device.

Figure 4:
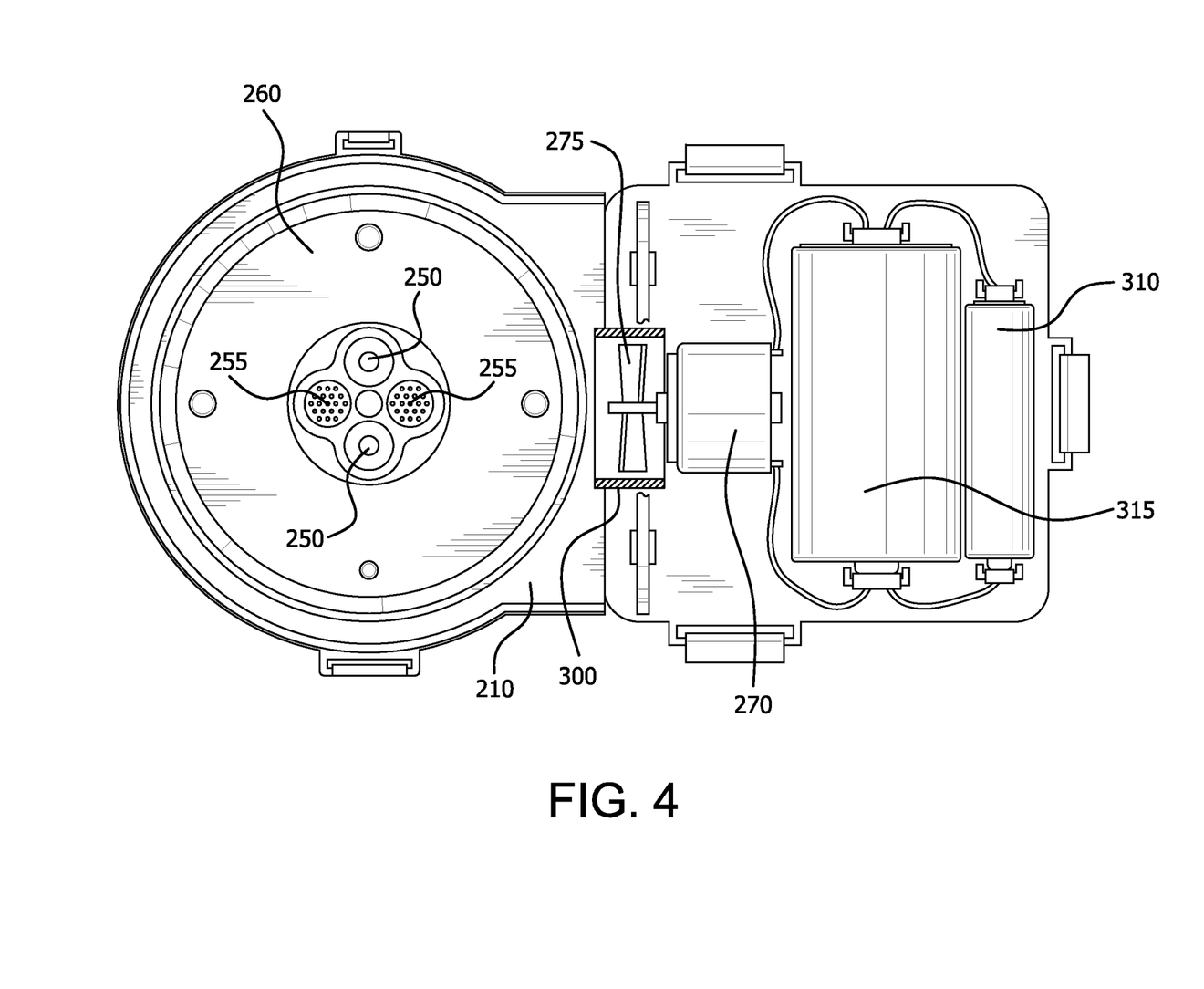
FIG. 4 is a top view of the base member of the device of FIG. 3.

FIG. 4 is a top view of the base member of the device of FIG. 3. As is noted above, bed bug capturing device 210 comprises ampoule receiving means 250 which are located within trap area 260. Fan 270 is powered by batteries 310 and 315. Baffle 300 surrounds propeller 275 to ensure a steady flow of air. Air generated by the turning of propeller 275 passes through channel 280 (see FIG. 3) and through air holes 255 into the air space above. Molecules diffusing out of ampoules inserted into receiving means 250 are then moved out of the trap by such moving air current.

It is noted that in the embodiment shown in FIGS. 3 and 4 that two ampoule receiving means are shown. In a preferred embodiment, one of these receiving means would be filled with an ampoule containing butyric acid in nonane; and the other would be filled with one or more aldehydes (such as octenal or decenal) in decane.

Figure 5:
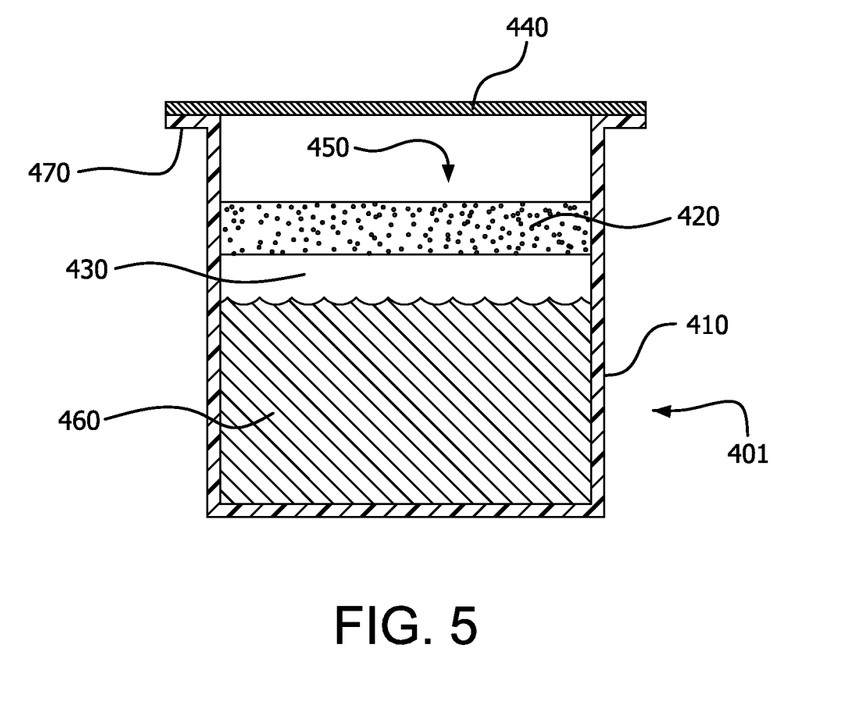
FIG. 5 is a cross-sectional view of a further embodiment of this invention wherein the porous diffusion member is planar in cross-section.

FIG. 5 is a cross-sectional view of a further embodiment of the ampoule of this invention wherein the porous diffusion member is planar in cross-section. Ampoule 401 is composed of outer shell 410 which defines at least one opening. Porous diffusion member 420, which is planar in cross-section, is inserted within outer shell 410 and defines interior reservoir 430. Film member 440 is disposed across the at least one opening defined by outer shell 410, such that air space 450 is defined between film member 440 and porous diffusion member 420. Outer shell 410 comprises flange 470 which increases the surface area available for sealing film member 440 to outer shell 410. Liquid 460, which comprises one or more volatile chemicals, is disposed within internal reservoir 430.

Porous diffusion member 420 is configured such that molecules of liquid 460 can only enter into air space 450 via diffusion through porous diffusion member 420. Specifically, such diffusion member 420 is configured such that liquid 460 cannot leak directly into air space 450, e.g., by passing between diffusion member 420 and outer shell 410.

Volatile molecules contained in liquid 460 will diffuse through porous diffusion member 420 and into air space 450. In embodiments in which film member 440 is a permeable membrane, such molecules may diffuse directly through film member 440 and into the ambient environment.

In embodiments in which film member 440 is impermeable to such molecules, one or more holes (not shown) may be created in film member 440 which will permit the release of such molecules from air space 450 into the ambient environment. By determining the precise dimensions of such one or more holes, such release rate may be set at a predetermined rate.

The following examples are intended to further illustrate the invention but are not intended to limit the scope of the invention in any manner.

EXAMPLES

Example 1

Attraction Assays

Assay arenas were made from 150×15 mm plastic Petri dishes (VWR#25384-326) containing a 125 mm piece off qualitative filter paper (VWR#28320-100) glued to the bottom using 3M Super 77® multipurpose spray adhesive. An 80 mm hole was cut into the lid and a 500 um mesh Nytex® screen (Bioquip, #7293B) was glued to cover the opening using quick epoxy. Fresh bottom dishes were used in each assay. For these experiments 2.4 cm filter paper was folded to create a tent and was treated with either a control solution (10 microliters of silicon oil) or 10 microliters of the experimental chemical diluted in silicon oil. Ten bed bugs per test were used. Day cycling bed bugs (*Cimex lectularius*), 12 hour light: 12 hour dark (7 AM On: 7 PM Off) light cycle, were incubated and evaluated under normal room lighting conditions at room temperature. Readings were taken at 1 hour intervals from the release of bedbugs for 4 hours. The number of bed bugs under the control filter paper disk and the number of bed bugs under the experimental filter paper disk were recorded. The test chemical was considered to be an attractant if the number of bed bugs under the experimental filter disk was greater than the number under the control filter disk. Table 1 below summarizes the experimental data, the experimental tests considered as attractants are in bold.

TABLE 1

Bed Bug Attraction to Aldehydes

| Treatment Rate *(ppm) | 1 Hour | | 2 Hour | | 3 Hour | | 4 Hour | |
|---|---|---|---|---|---|---|---|---|
| | Control | Exp | Control | Exp | Control | Exp | Control | Exp |
| Hexenal | | | | | | | | |
| *10000 | 3 | 0 | 4 | 1 | 4 | 1 | 4 | 1 |
| 1000 | 1 | 6 | 1 | 7 | 1 | 9 | 1 | 9 |
| 100 | 0 | 6.5 | 0 | 8 | 0 | 9 | 0 | 8.5 |
| 10 | 9 | 3 | 5 | 3.5 | 5 | 4 | 5 | 5.5 |
| 1 | 0 | 4 | 0 | 6 | 0 | 6.5 | 0.5 | 6 |
| Octenal | | | | | | | | |
| *10000 | 0 | 2 | 2 | 2 | 3 | 2 | 4 | 4 |
| 1000 | 1.5 | 5 | 3 | 4.5 | 3 | 5 | 3 | 5 |
| 100 | 0 | 5 | 1 | 6.5 | 1 | 7 | 1 | 6.5 |
| 10 | 4 | 2 | 4.5 | 4 | 5 | 4.5 | 5.5 | 4 |
| 1 | 5 | 1 | 4.5 | 2 | 5.5 | 3.5 | 3.5 | 5 |

*10000 ppm rate for Hexenal and Octenal was one test; all others were an average of two tests.
Hexenal is trans-hex-2-en-1-al
Octenal is trans-oct-2-en-1-al The above data indicate that bed bug attractants such as hexenal and octenal will be most effective at concentrations in the hundreds through thousands of ppm; and that when employed at higher concentrations such "attractants" will exhibit a repellent effect.

Example 2

A test arena was constructed from a 60×40×22 cm (L:W:H) polystyrene container. A 60×40 cm piece of filter paper was glued on the bottom to provide a walking surface for the bedbugs. At one end of the test arena, a triangular piece of plastic (16 cm high×25 cm long) was glued to the middle of the side and bottom of the container to create a partition of equal area on either side of the partition. Deadfall insect trap bases were placed in both the control and the experimental zones.

The control trap did not contain any lure, while the test trap contained two one hundred micro Liter pipettes. One end of each pipette (Drummond Wiretrol 100 µL) was sealed with parafilm while the other end was left open. The first pipette contained a 300 ppm solution containing Hexenal and Octenal in a 75:25 ratio, prepared by dissolving the aldehydes in decane. The second pipette contained a 200 ppm solution of butyric acid in nonane.

Fifty bed bugs (*Cimex lectularius*) were entrapped within an inverted 90 mm Petri dish at a position furthest from the control and experimental zones until bed bugs were quiescent. Removal of the Petri dish started the experiment. After 2 hours it was observed that 20-30 bedbugs were located within 5-15 cm of the test trap, but that no bed bugs were closer than 5 cm to the trap. This observation supports the conclusion that these attractants will effectively attract bed bugs at a given concentration, but will repel them if present at too high a concentration.

Example 3

In order to show the ability of the ampoules of this invention to release aqueous formulations at a consistent rate over an extended period of time, the following experiment was conducted. Ampoules were constructed employing a cylindrical outer shell made of polyethylene, and having a height of 14.5 mm and a diameter of 11 mm. These outer shells were filled with 300 microliters of nonane. A cylindrical porous diffusion member, made of ultra high molecular weight polyethylene, was disposed inside the outer shell in a contraposition such that the volatile liquid was contained in the interior reservoir formed by such diffusion member. The opening of the outer shell was then thermally sealed with an aluminum film member, leaving a head space of about 2-2.5 mm between the bottom portion of the film member and the top of the diffusion member. A hole having a diameter of about 0.23 mm was made in the aluminum film by puncturing it with a needle. As a comparison, identical ampoules without the porous diffusion member were also prepared, except that 450 microliters (323 milligrams) of nonane were added. The ampoules were stored under ambient conditions and the release of the volatile liquid determined by weight measurement at the time intervals listed below. The results of such testing are presented below:

| Elapsed Time (Hrs) | Without diffusion member Solvent loss(mg) | With diffusion member Solvent loss(mg) |
|---|---|---|
| 0.0 | 0.0 | 0.0 |
| 4.0 | 0.0 | 0.0 |
| 22.0 | 1.8 | 1.8 |
| 95.0 | 35.1 | 20.6 |
| 117.5 | 49.7 | 27.1 |
| 141.5 | 64.7 | 34.8 |
| 166 | 79.2 | 42.3 |
| 189 | 92.3 | 48.5 |
| 262 | 128.0 | 70.3 |
| 285.5 | 138.5 | 77.3 |
| 309.5 | 148.8 | 84.4 |
| 334 | 163.7 | 92.2 |
| 358 | 171.3 | 99.0 |
| 430 | 201.2 | 117.6 |

The above data show that a linear release rate for highly volatile compounds such as $C_8$-$C_{12}$ alkanes can be obtained employing the ampoules of this invention. Further, such data show that greatly enhanced release times can be achieved employing the ampoules of this invention relative to those which do not employ a porous diffusion member.

What is claimed is:

1. An ampoule for the storage and dispersion of a volatile liquid comprised of:
   a) an outer shell composed of an impermeable material and defining at least one opening;
   b) a porous diffusion member composed of a sintered, porous synthetic resin having a controlled porosity and having omnidirectional interconnecting pores, said porous diffusion member defining an internal reservoir therein which is positioned inside said outer shell;
   c) a volatile liquid contained within said internal reservoir so as to substantially encapsulate the volatile liquid; and
   d) a film member, which is impermeable to the volatile liquid, adhered to said outer shell and covering said at least one opening; wherein said film member is disposed such that an air space is present between said porous diffusion member and said film member; and wherein said porous diffusion member is configured such that molecules of the volatile liquid can only enter into said air space via diffusion through said porous diffusion member;
   characterized in that when one or more holes having a dimension or dimensions and a location or locations, respectively, is or are created in said film member, said volatile liquid is released at a constant rate which is regulated by the dimension or dimensions and location or locations of said one or more holes.

2. The ampoule of claim 1 wherein the volatile liquid comprises at least one member selected from the group consisting of perfumes, air fresheners, aroma therapy components, pesticides, repellants and pharmaceuticals.

3. The ampoule of claim 1 wherein the volatile liquid comprises a bed bug attractant.

4. The ampoule of claim 3 wherein said attractant is dissolved in a $C_8$-$C_{12}$ alkane.

5. The ampoule of claim 3 wherein said attractant comprises at least one member selected from the group consisting of hexenal, octenal and butyric acid.

6. The ampoule of claim 1 wherein the outer shell is composed of polyethylene terephthalate.

7. The ampoule of claim 1 wherein the film member is composed of aluminum.

8. The ampoule of claim 1 wherein the porous diffusion member is composed of ultra high molecular weight polyethylene.

9. The ampoule of claim 1 wherein the porous diffusion member is fabricated from a member of the group consisting of high-density polyethylene, low-density polyethylene, ultra-high molecular weight polyethylene, polypropylene and polyvinylidene fluoride.

* * * * *